(12) United States Patent
Vallone

(10) Patent No.: US 10,146,400 B2
(45) Date of Patent: Dec. 4, 2018

(54) ICON-BASED USER INTERFACES

(71) Applicant: Anthony J. Vallone, North Canton, OH (US)

(72) Inventor: Anthony J. Vallone, North Canton, OH (US)

( * ) Notice: Subject to any disclaimer, the term of this patent is extended or adjusted under 35 U.S.C. 154(b) by 1427 days.

(21) Appl. No.: 13/730,075

(22) Filed: Dec. 28, 2012

(65) Prior Publication Data

US 2013/0145317 A1   Jun. 6, 2013

Related U.S. Application Data

(63) Continuation-in-part of application No. 11/519,036, filed on Sep. 11, 2006, now Pat. No. 8,370,175.

(51) Int. Cl.
| | |
|---|---|
| *G06Q 10/10* | (2012.01) |
| *G06F 3/0481* | (2013.01) |
| *A61B 5/00* | (2006.01) |
| *G06Q 50/22* | (2018.01) |

(52) U.S. Cl.
CPC ........ *G06F 3/04817* (2013.01); *A61B 5/7435* (2013.01); *A61B 5/7475* (2013.01); *G06Q 10/10* (2013.01); *G06Q 50/22* (2013.01)

(58) Field of Classification Search
USPC ........................................................ 705/2, 3
See application file for complete search history.

(56) References Cited

U.S. PATENT DOCUMENTS

| | | | |
|---|---|---|---|
| 7,957,984 B1* | 6/2011 | Vallone ............. | G06Q 50/22 705/2 |
| 2002/0140746 A1* | 10/2002 | Gargi ............... | G06F 3/0483 715/853 |
| 2006/0013462 A1* | 1/2006 | Sadikali ............ | G06F 19/321 382/132 |
| 2007/0152958 A1* | 7/2007 | Ahn ................. | G06F 3/0219 345/156 |
| 2011/0060666 A1* | 3/2011 | Gromek ............ | G06F 3/0482 705/27.2 |
| 2012/0094753 A1* | 4/2012 | Petri ................ | G07F 17/3211 463/30 |

* cited by examiner

Primary Examiner — Robert W Morgan
Assistant Examiner — Edward B Winston, III
(74) Attorney, Agent, or Firm — Black, McCuskey, Souers & Arbaugh, LPA

(57) ABSTRACT

Within the field of computing, many user interfaces may present a set of records. Presented herein are user interfaces that may be advantageous in some scenarios, involving the presentation of a stack of unit boxes having a stack order. A current unit box may present a record filling an entirety of the display and including at least two icons respectively depicting an item of information in the record. The device may also accept a gesture from a user along a first axis, such that a gesture in a forward direction along the first axis (e.g., tapping a right half of a touch-sensitive display) visual transitions to a next unit box in the stack order, and a gesture in a direction opposite the forward direction (e.g., tapping a left half of the display) along the first axis visually transitions to a preceding unit box in the stack order.

23 Claims, 9 Drawing Sheets

50% UNIT BOX TRANSITION

ICON-BASED USER INTERFACES

RELATED APPLICATION

This application is a continuation-in-part of U.S. patent application Ser. No. 11/519,036, filed on Sep. 11, 2006 and entitled "Icon-Based Healthcare Management System," the entirety of which is incorporated by reference herein.

BACKGROUND

The generation and maintenance of patient healthcare records can be a time-consuming task. In the healthcare industry, the current emphasis placed on cost containment has resulted in a higher volume of patients being seen during a given period of time. In healthcare and other fields, information may be stored as a set of records respectively comprising at least two items of information. The set of icon-generated records may be sorted in an order, e.g., according to a date field provided as one of the items of information, and the user may be permitted to navigate through the set of ordered records using various user interface techniques in efforts to create, organize, update, or remove information.

SUMMARY

This Summary is provided to introduce a selection of concepts in a simplified form that are further described below in the Detailed Description. This Summary is not intended to identify key factors or essential features of the claimed subject matter, nor is it intended to be used to limit the scope of the claimed subject matter.

While the presentation of records as an ordered set may be achieved through many user interface techniques, it may be appreciated that some user interfaces may present some advantages as compared with other user interfaces. For example, the presentation of information in a manner that is independent of a particular language may improve the user's understanding of the presented information, e.g., when the user is not fluent in the language in which the information was recorded. Additionally, when the user transitions among various records in the record set, depicting a transition between the records may improve the user's understanding of the consequences of the transition request. Such techniques may be used, e.g., to present an icon-based healthcare patient care system including an association data store that stores association information between a category and icon(s). Such systems may further comprise a patient care logic configured to provide icon-based healthcare information based on selection information received from a user.

In view of these techniques, presented herein are user interfaces involving a presentation of a stack of unit boxes on a display of a device. In accordance with these techniques, at a particular location in the stack order of the unit boxes, a current unit box is presented that fills the display of the device and includes at least two icons that respective depict an item of the unit box. For example, a particular icon may represent an object such as a wheelchair and/or when combined with another icon (e.g., a sitting figure icon) represents the activity of transferring from the wheelchair.

Additionally, when the user may access unit box information by initiating a forward gesture associated with a first axis in a forward direction (e.g., tapping on a right half of the unit box, or swiping horizontally to the left across the display to cause the information to navigate in a rightward direction), the device may navigate from the current unit box to a next unit box following the current unit box in the stack order, and may display a transition from the current unit box to the next unit box. Conversely, when the user initiates a backward gesture associated with the first axis that is opposite the forward direction (e.g., tapping on a left half of the unit box, or swiping horizontally to the right across the display to cause the information to navigate in a leftward direction), the device may navigate from the current unit box to a preceding unit box that is before the current unit box in the stack order, and may display a transition from the current unit box to the preceding unit box. The presentation of unit boxes in this manner, and the arrangement of such with navigations represented by visual transitions, may facilitate the user's understanding of the relationships of a first presented unit box and a subsequently presented unit box.

To the accomplishment of the foregoing and related ends, the following description and annexed drawings set forth certain illustrative aspects and implementations. These are indicative of but a few of the various ways in which one or more aspects may be employed. Other aspects, advantages, and novel features of the disclosure will become apparent from the following detailed description when considered in conjunction with the annexed drawings.

DETAILED DESCRIPTION

Figure 1:
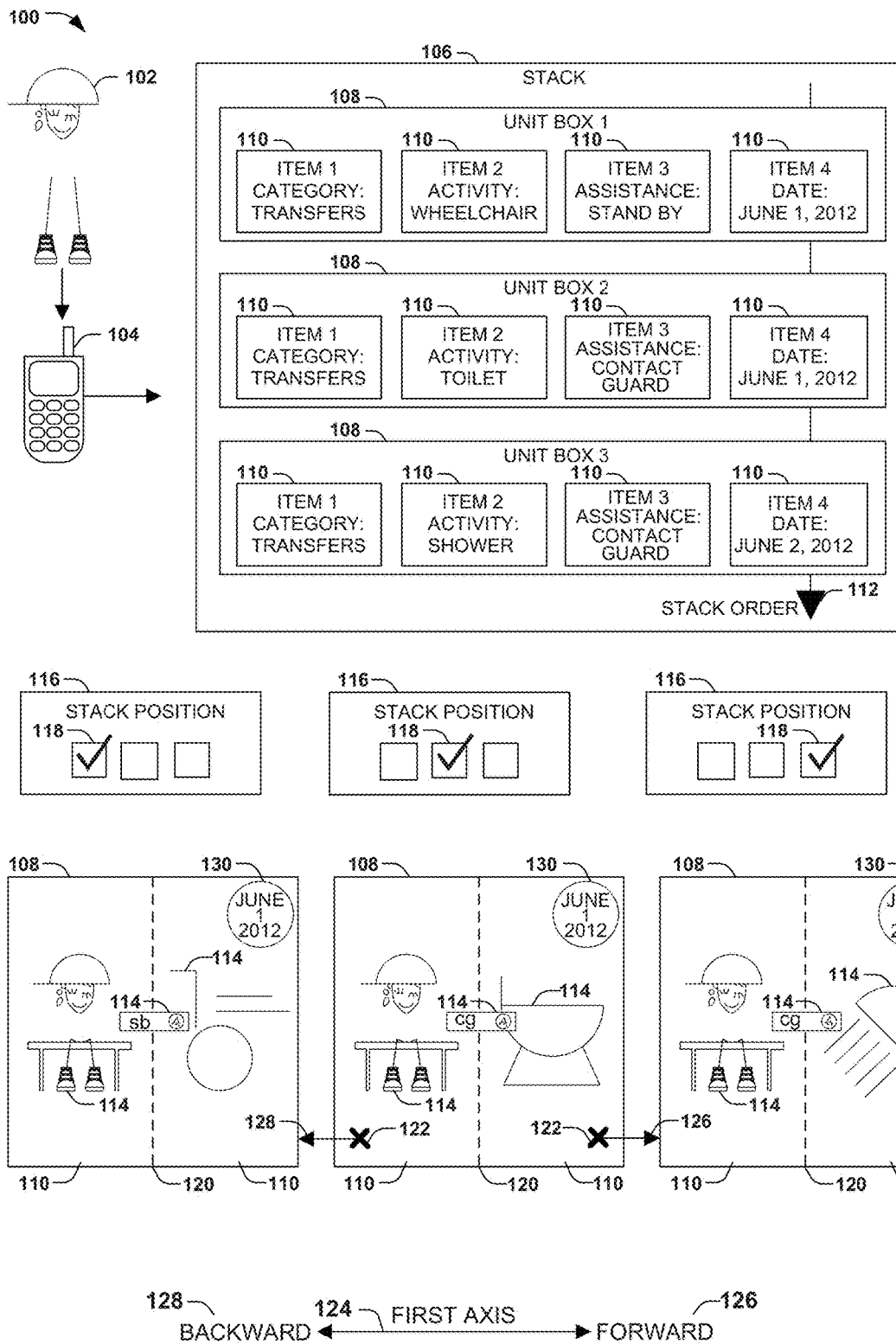
FIG. 1 is an illustration of an exemplary scenario featuring a presentation of a set of unit boxes in a stack order on a device in accordance with the techniques presented herein.

The claimed subject matter is now described with reference to the drawings, wherein like reference numerals are used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are shown in block diagram form in order to facilitate describing the claimed subject matter.

A. Definitions

The following includes definitions of selected terms employed herein. The definitions include various examples and/or forms of components that fall within the scope of a term and that may be used for implementation. The examples are not intended to be limiting. Both singular and plural forms of terms may be within the definitions.

As used in this application, the term "computer component" refers to a computer-related entity, either hardware, firmware, software, a combination thereof, or software in execution. For example, a computer component can be, but is not limited to being, a process running on a processor, a processor, an object, an executable, a thread of execution, a program, and a computer. By way of illustration, both an application running on a server and the server can be computer components. One or more computer components can reside within a process and/or thread of execution and a computer component can be localized on one computer and/or distributed between two or more computers.

"Computer-readable storage device", as used herein, refers to a medium that participates in directly or indirectly providing signals, instructions and/or data. A computer-readable medium may take forms, including, but not limited to, non-volatile media, volatile media, and transmission media. Non-volatile media may include, for example, optical or magnetic disks and so on. Volatile media may include, for example, semiconductor memories, dynamic memory and the like. Transmission media may include coaxial cables, copper wire, fiber optic cables, and the like. Common of computer-readable storage devices include, but are not limited to, a floppy disk, a flexible disk, a hard disk, a magnetic tape, other magnetic medium, a CD-ROM, other optical medium, punch cards, paper tape, other physical medium with patterns of holes, a RAM, a ROM, an EPROM, a FLASH-EPROM, or other memory chip or card, a memory stick, and other media from which a computer, a processor or other electronic device can read.

"Data store", as used herein, refers to a physical and/or logical entity that can store data. A data store may be, for example, a database, a table, a file, a list, a queue, a heap, a memory, a register, and so on. A data store may reside in one logical and/or physical entity and/or may be distributed between two or more logical and/or physical entities.

"Icon," as used herein, refers to a graphic symbol and/or word whose form visually depicts its meaning. An icon may include one or more words or symbols, but primarily conveys information through the depiction of information rather than via a literal text.

"Logic", as used herein, includes but is not limited to hardware, firmware, software and/or combinations of each to perform a function(s) or an action(s), and/or to cause a function or action from another logic, method, and/or system. For example, based on a desired application or needs, logic may include a software controlled microprocessor, discrete logic like an application specific integrated circuit (ASIC), an analog circuit, a digital circuit, a programmed logic device, a memory device containing instructions, or the like. Logic may include one or more gates, combinations of gates, or other circuit components. Logic may also be fully embodied as software. Where multiple logical logics are described, it may be possible to incorporate the multiple logical logics into one physical logic. Similarly, where a single logical logic is described, it may be possible to distribute that single logical logic between multiple physical logics.

"Query", as used herein, refers to a semantic construction that facilitates gathering and processing information. A query might be formulated in a database query language like structured query language (SQL) or object query language (OQL). A query might be implemented in computer code (e.g., C#, C++, Javascript) that can be employed to gather information from various data stores and/or information sources.

"Software", as used herein, includes but is not limited to, one or more computer or processor instructions that can be read, interpreted, compiled, and/or executed and that cause a computer, processor, or other electronic device to perform functions, actions and/or behave in a desired manner. The instructions may be embodied in various forms like routines, algorithms, modules, methods, threads, and/or programs including separate applications or code from dynamically linked libraries. Software may also be implemented in a variety of executable and/or loadable forms including, but not limited to, a stand-alone program, a function call (local and/or remote), a servlet, an applet, instructions stored in a memory, part of an operating system or other types of executable instructions. It will be appreciated by one of ordinary skill in the art that the form of software may be dependent on, for example, requirements of a desired application, the environment in which it runs, and/or the desires of a designer/programmer or the like. It will also be appreciated that computer-readable and/or executable instructions can be located in one logic and/or distributed between two or more communicating, co-operating, and/or parallel processing logics and thus can be loaded and/or executed in serial, parallel, massively parallel and other manners.

Suitable software for implementing the various components of the example systems and methods described herein include programming languages and tools like Java, Pascal, C#, C++, C, CGI, Perl, SQL, APIs, SDKs, assembly, firmware, microcode, and/or other languages and tools. Software, whether an entire system or a component of a system, may be embodied as an article of manufacture and maintained or provided as part of a computer-readable medium as defined previously. Another form of the software may include signals that transmit program code of the software to a recipient over a network or other communication medium. Thus, in one example, a computer-readable medium has a form of signals that represent the software/firmware as it is downloaded from a web server to a user. In another example, the computer-readable medium has a form of the software/firmware as it is maintained on the web server. Other forms may also be used.

"Stack," as used herein, includes but is not limited to a one-dimensional array of records ordered according to a stack order. A stack may be navigated, e.g., via a stack pointer that indicates a current record, and which may be altered to indicate the preceding or succeeding record in the stack order. Records may be added or removed through forward and back operations.

"User", as used herein, includes but is not limited to one or more persons, software, computers or other devices, or combinations of these.

B. Introduction

Within the field of computing, many scenarios involve the recording of a set of records for a topic, such as a set of descriptors for a health record of an individual. In such scenarios, the records may be stored and presented in various ways, such as a set of text entries in a table with respective rows indicating observations recorded by a healthcare provider.

Traditionally, patient healthcare information has been maintained in text-based handwritten and/or typed notes as currently seen with the advent of computers. Limitations in this system persist including an inordinate amount of user time that is spent in locating, reading and/or comprehending information. In addition, the current system is restricted due to formatting variability of information in addressing visit notes and/or reports. Additionally, conventional systems often have difficulty "shepherding" information from creation until discharge, thereby resulting in a decreased foundation when building subsequent visit notes and reports. With conventional systems, the user is left to their memory and/or time restraints in searching for and interpreting prior notes as current activities or conditions are addressed.

C. Present Disclosure

Presented herein are techniques for creating, presenting, accessing, and removing records in a record set as a stack of unit boxes having a stack order. Respective unit boxes may represent, e.g., the fields of a record in a health record of an individual, and may represent instances of observations about the health state of the individual; of activities prescribed for and/or performed for or by the individual; and of the provision of healthcare to the individual by a healthcare provider. The present techniques provide user interfaces for accessing the unit boxes in various ways, e.g., in order to provide different mechanisms for efficiently and intuitively navigating among the unit boxes and providing information to assist in the creation, updating, discharging, and removal thereof. Such user interfaces may be usable in a wide variety of scenarios; i.e., while the examples presented herein involve health records of an individual, other types of records comprising a set of unit boxes may also be displayed according to the techniques presented herein.

FIG. 1 presents an illustration of an exemplary scenario 100 featuring a user 102 interacting with a device 104 that is configured to present a health record as a stack 106 of unit boxes 108 that respectively comprise at least two items 110, such as descriptors of the record represented by the unit box 108. For example, in a health record of an individual, a unit box 110 may comprise a category, such as a "transfers" category; an activity, such as an individual's action in transferring from a wheelchair, toilet, or shower chair; a proficiency, such as the individual's level of assistance required to perform the activity; and a date 130 on which the activity was observed and/or measured. In accordance with these techniques, the unit boxes 108 are presented on a display of the device 104 according to a stack order 112 of the stack 106, e.g., according to an ordering of the categories represented by the unit boxes 108 or a date 130 on which the unit box 108 was created or accessed. The present techniques involve selecting a current unit box 118 at a current stack position 116 within the stack 106, and presenting the unit box 108 on the display in a manner that fills the display (e.g., substantially meeting the edges of the display of the device 104). Respective items 110 of the current unit box 118 may be depicted by displaying an icon 114 at a position on the display of the device 104 for the item 110 presented. For example, in the exemplary scenario 100 of FIG. 1, a unit box 108 may comprise a first icon 114 depicting the category (e.g., an icon indicating a "transfers" category) and a second icon 114 depicting an activity (e.g., the individual's action in transferring from a wheelchair, toilet, or shower chair). Additional information may be provided through normalized or stylized text, e.g., a proficiency indicator presented as text and indicating the proficiency of the individual in performing the activity. Respective icons 114 may be presented at specific positions on the display for each unit box 108 in order to establish a consistent presentation of information (e.g., the categories icon may consistently be presented on the left half of the display; the activities icon may consistently be presented on the right half of the display; and the proficiency indicator may be presented at the center of the display).

As further provided in the exemplary scenario 100 of FIG. 1, the device 104 may be configured to enable navigation of the current unit box 118 within the stack order 112 of the stack 106. To this end, the device 104 may define a first axis 124 having a forward direction 126 and a backward direction 128 (e.g., a lateral axis of the display of the device 104 where rightward activities indicate the forward direction 126 and leftward activities indicate the backward direction 128). The device 104 may be configured to, upon receiving a forward gesture 122 associated with the first axis 124 and in the forward direction 126 (e.g., a tap to drill down at a position to the right of a midline 120 of the unit box 108, or a leftward swipe that causes the information to navigate in a rightward direction), the device 104 may navigate to the next unit box 108 in the stack order 112 of the stack 106 and present the next unit box 108 on the display of the device 104. Conversely, upon receiving a backward gesture 122 associated with the first axis 124 and opposite the forward direction 126 (e.g., a tap to drill up at a position to the left of the midline 120 of the unit box 108, or a rightward swipe that causes the information to navigate in a leftward direction), the device 104 may navigate to the preceding unit box 108 in the stack order 112 of the stack 106 and present the preceding unit box 108 on the display of the device 104. The navigation may also be associated with animations (e.g., presenting a forward slide transition along the first axis 124 upon receiving a forward gesture and presenting a backward slide transition along the first axis 124 upon receiving a backward gesture) to assist the user in understanding the navigation within the stack order 112. In this manner, the device 104 may be configured to present and enable navigation within the stack 106 of unit boxes 108 according to the stack order 112.

These techniques for presenting information may have several advantages with respect to other presentations. For example, an icon-based health care management system "shepherds" information associated with an activity once it is stored as a unit box in the stack, thereby complementing subsequent visit(s), as the activit(ies) information cycles in a closed system requiring it to be addressed by either updating, skipping and/or removing as per user's choice. Once entry of information associated with the activity has been completed, information can be stored in a patient care data store. Entry of information can be repeated and stored, as necessary (e.g., clone activity). Patient care information is stored in the patient care data store in a standardized manner thus facilitating retrieval of the patient care information. For example, a user can retrieve and review historical icon-based information such as when transferring from the wheelchair, over its duration. In doing so, an advantage gained is in determining if the activity is improving, declining or remaining static. In addition, a "critical pathway" may be developed as per Medicare's specifications in addressing the frequency and/or quality of an activity or condition over a prescribed duration. The icon-based user interface may also enable a comparatively simple and intuitive navigational system that may be cognizable to users 102 with little training. The language-independent presentation of information through the use of icons 114 depicting the items 110 of the unit boxes 108 may enable the communication of information in a manner that is understandable to the user 102 and communicable between users 102 irrespective of native languages, understanding of technical terms, or cultural conventions. Moreover, this navigational user interface may enable the inclusion of additional features for the creation, organization, annotation, accessing, updating, and removing the unit boxes 108 of the stack 106 in a manner that are consistent with the user interfaces and environment provided herein.

D. Exemplary Embodiments

Figure 2:
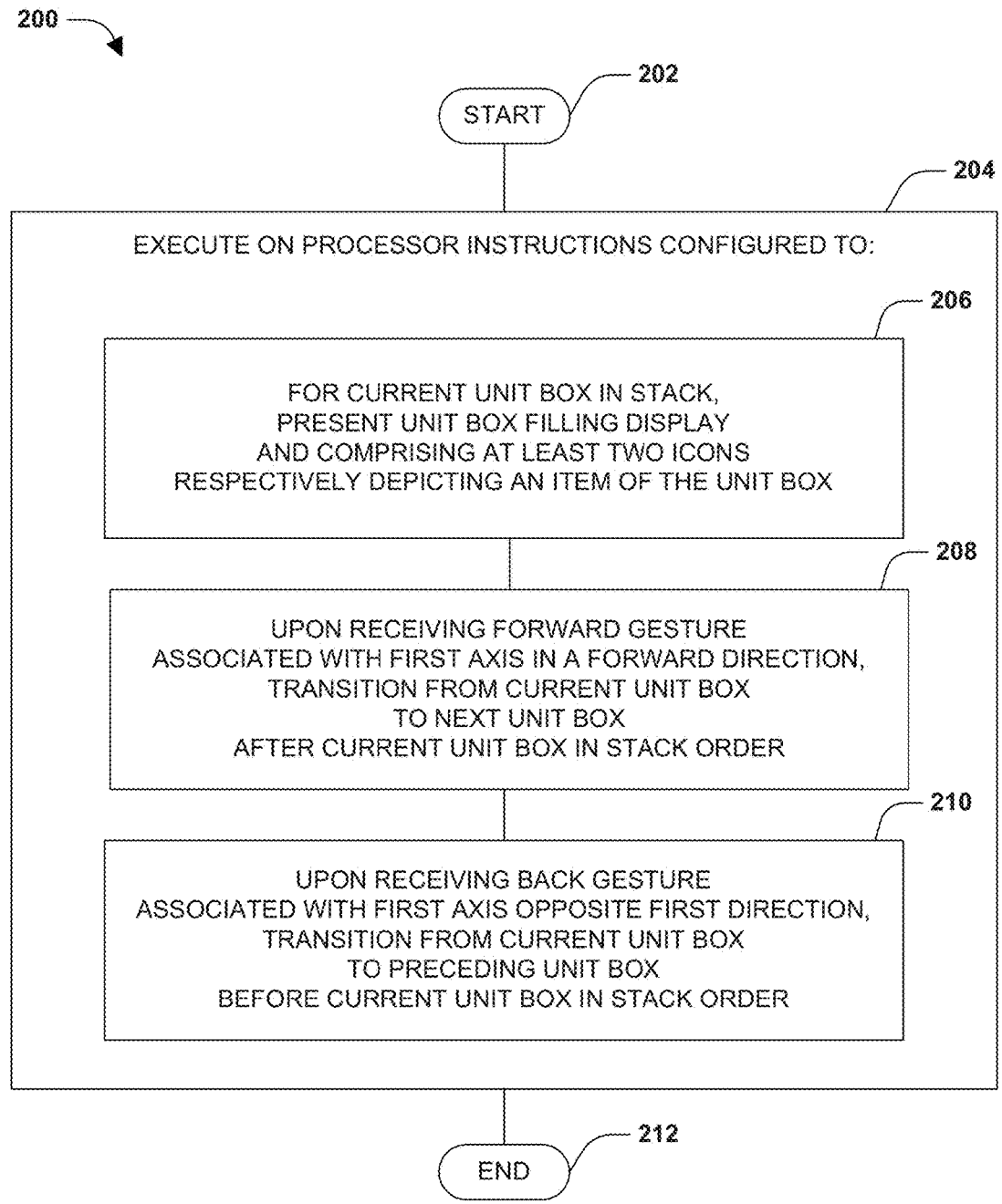
FIG. 2 is a flow diagram depicting in accordance with the techniques presented herein.

FIG. 2 presents an illustration of an exemplary method 200 of presenting the stack 106 of unit boxes 108 according to the techniques presented herein. This exemplary method 200 may be implemented, e.g., as a set of instructions stored in a memory component of a device 104 (e.g., a memory circuit, a platter of a hard disk drive, a solid-state storage device, or a magnetic or optical disc) having a memory storing an icon set, such that, when the instructions are executed by a processor of the device 104, the device 104 functions according to the techniques presented herein. The exemplary method 200 begins at 202 and involves executing 204 the instructions on the processor. In particular, the instructions are configured to, for a current unit box 118 in the stack 106, present 206 a unit box 108 filling the display of the device 104 and comprising at least two icons 114 respectively depicting an item 110 of the unit box 108. The instructions are also configured to, upon receiving a forward gesture associated with a first axis 124 in a forward direction 126 (e.g., a rightward swipe laterally across the display of the device 104), transition 208 from the current unit box 118 to a next unit box after the current unit box 118 in the stack order 112. The instructions are also configured to, upon receiving a backward gesture associated with the first axis 124 and opposite the forward direction 126, transition 210 from the current unit box 118 to a preceding unit box before the current unit box 118 in the stack order 112. In this manner, the exemplary method 200 causes the device 104 to function according to the techniques presented herein, and so ends at 212.

Figure 3:
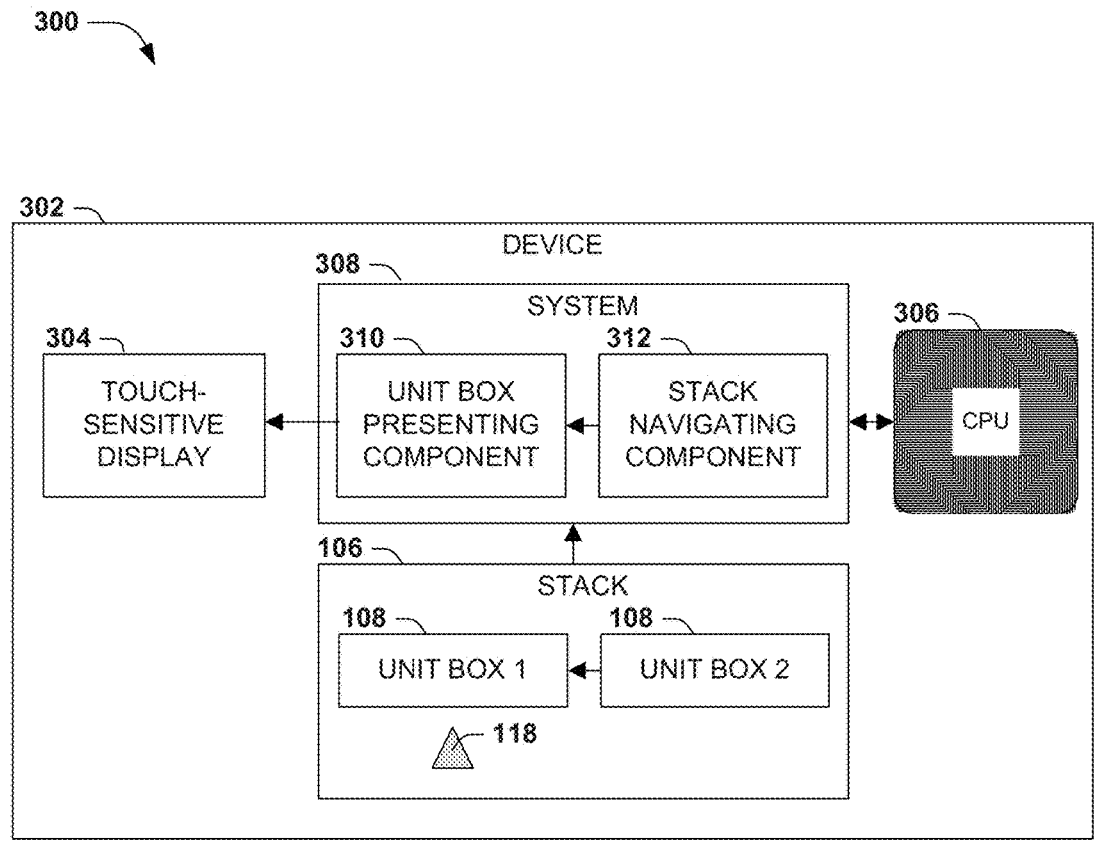
FIG. 3 is a component block diagram of an exemplary component architecture of a device configured to according to the techniques presented herein.

FIG. 3 presents an illustration of an exemplary scenario 300 featuring an exemplary system 308 for presenting a stack 106 of unit boxes 108 on a display of a device 104 having a touch-sensitive display 304 and a memory storing an icon set. Respective components of the exemplary system 308 may be implemented, e.g., as a set of instructions stored in a memory of the device 302 that, when executed on the processor 306, provide a set of interoperating components that together cause the device 302 to function according to the techniques presented herein. The exemplary system 308 includes a unit box presenting component 310 that, for a current unit box 118 in the stack 106, presents on the touch-sensitive display 304 a unit box 108 filling the display 304 and comprising at least two icons 114 respectively depicting an item 110 of the unit box 108. The exemplary system 308 also includes a stack navigating component 312 that, upon receiving a forward gesture 122 associated with a first axis 124 in a forward direction 126, transitions from the current unit box 118 to a next unit box 108 after the current unit box 118 in the stack order 112; and, upon receiving a backward gesture 122 associated with the first axis 124 opposite the forward direction 126, transitions from the current unit box 118 to a preceding unit box 108 before the current unit box 118 in the stack order 112. In this manner, the exemplary system 308 enables the presentation and navigation within the stack 106 of unit boxes 108 in accordance with the techniques presented herein.

Still another embodiment involves a computer-readable medium comprising processor-executable instructions configured to apply the techniques presented herein. Such computer-readable media may include, e.g., computer-readable storage media involving a tangible device, such as a memory semiconductor (e.g., a semiconductor utilizing static random access memory (SRAM), dynamic random access memory (DRAM), and/or synchronous dynamic random access memory (SDRAM) technologies), a platter of a hard disk drive, a flash memory device, or a magnetic or optical disc (such as a CD-R, DVD-R, or floppy disc), encoding a set of computer-readable instructions that, when executed by a processor of a device, cause the device to implement the techniques presented herein. Such computer-readable media may also include (as a class of technologies that are distinct from computer-readable storage media) various types of communications media, such as a signal that may be propagated through various physical phenomena (e.g., an electromagnetic signal, a sound wave signal, or an optical signal) and in various wired scenarios (e.g., via an Ethernet or fiber optic cable) and/or wireless scenarios (e.g., a wireless local area network (WLAN) such as WiFi, a personal area network (PAN) such as Bluetooth, or a cellular or radio network), and which encodes a set of computer-readable instructions that, when executed by a processor of a device, cause the device to implement the techniques presented herein.

Figure 4:
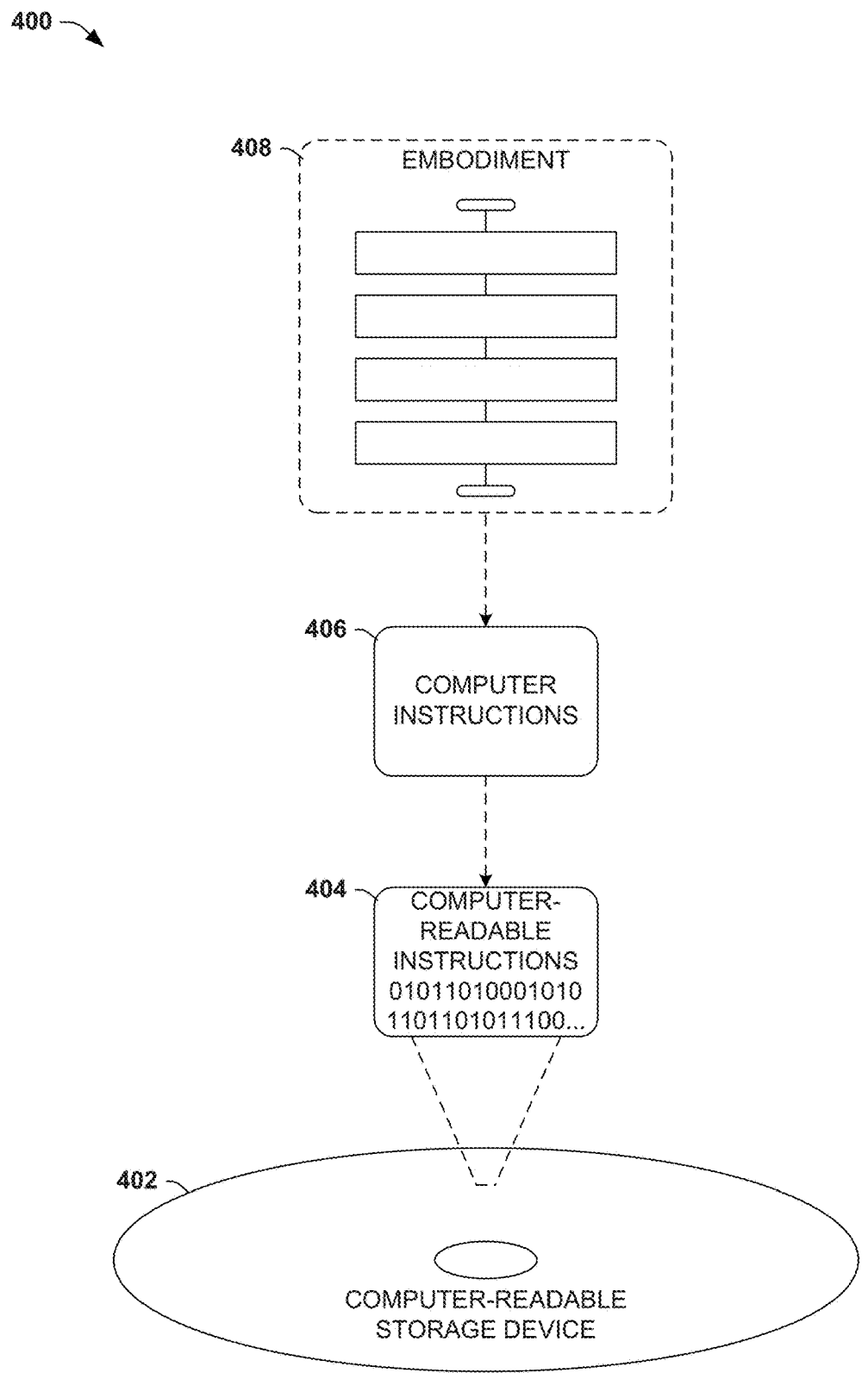
FIG. 4 is an illustration of an exemplary nonvolatile computer-readable storage device encoding executable instructions configured to cause a device to operate according to the techniques presented herein.

An exemplary computer-readable medium that may be devised in these ways is illustrated in FIG. 4, wherein the implementation 400 comprises a computer-readable medium 402 (e.g., a CD-R, DVD-R, or a platter of a hard disk drive), on which is encoded computer-readable data 404. This computer-readable data 404 in turn comprises a set of computer instructions 406 configured to operate according to the principles set forth herein. In one such embodiment, the processor-executable instructions 406 may be configured to perform a method 508 of presenting a stack 106 of unit boxes 108 on a display 304 of a device 104, such as the exemplary method 200 of FIG. 2. Some embodiments of this computer-readable medium may comprise a computer-readable storage medium (e.g., a hard disk drive, an optical disc, or a flash memory device) that is configured to store processor-executable instructions configured in this manner. Many such computer-readable media may be devised by those of ordinary skill in the art that are configured to operate in accordance with the techniques presented herein.

E. Variations

The techniques provided herein may include variations in particular aspects, where some such variations may be advantageous with respect to other variations of these and other techniques.

E1. Scenarios

A first aspect that may vary among embodiments of these techniques involves the scenarios wherein such techniques may be utilized.

As a first variation of this first aspect, many types of general-purpose computing devices 104 may be utilized, including workstations, servers, tablets, mobile phones and other mobile communication devices, palmtop and laptop computers, personal digital assistants, and network appliances. These techniques may also be usable with specific-use devices 104, such as medical equipment and medication reminder devices.

As a second variation of this first aspect, the devices 104 may include many types of input, processing, and output components. For example, the icon-based healthcare management system may include a voice recognition engine. The voice recognition engine can be trained on a vocabulary associated with a particular healthcare application as spoken by a particular user. By using voice recognition, the user can be freed from the physical constraints of using a pointing device and/or computer keyboard to provide information to the icon-based healthcare management system. For example, with respect to the physical therapy application discussed previously, the voice recognition engine can be trained to recognize a user's spoken words for the categories "transfers", "bed mobility", "gait", "ambulation" and "activities of daily living" ("ADLs"). In some embodiments, patent identification information may be received with a pointing device and/or verbally; via text, numeric, and/or alphanumeric identifier; and/or via biometric information for purposes of identification (e.g., fingerprint, retinas, iris, and voice samples employed for identification purposes).

As a third variation of this first aspect, the navigational user interface may provide stacks 106 of unit boxes 108 representing many types of information. As a first example, the unit boxes 108 may comprise the records of a health record of an individual, and may represent, e.g., visit notes recorded by healthcare providers about the state of the individual; activities performed by or for the individual; and instances of the provision of healthcare to the individual by a healthcare provider, such as medical procedures performed for the individual; historic records of the health state of the individual; and goals of therapy for the individual. The user interface may present a plan of care (PCo) that the healthcare professional expects the patient to be versed in one or more orthostatic hypotension (decline in blood pressure) signs and symptoms in a given duration through instruction of the medical condition. Information stored in a patient care data store and/or a discharge data store can be employed to facilitate billing. For example, information can be retrieved from the patient care data store and/or the discharge data store, formatted (e.g., OASIS data specification) and transmitted (e.g., electronically) to an insurer and/or government agency (e.g., Medicare and/or Medicaid). As another example, the unit boxes 108 may represent instances of an exercise regimen of an individual, including previously performed instances and instances that are planned for the future. As a third example, the unit boxes 108 may represent service tasks to be performed by various individuals in various settings, such as cleaning activities to be performed by service agents in a hospitality service such as a hotel.

As a fourth variation, the device 104 may be configured for operation by many types of users 102. For example, the device 104 may be usable by healthcare providers; by an individual whose health history is represented as a stack 106 of unit boxes 108; by a caregiver or family member of the individual; by a healthcare administrator; or by a service agent in a service industry, such as home healthcare or hotel services. The device 104 may be adapted for such users 102 (e.g., by providing different user interfaces that enable a different set of functionality that is appropriate for the user 102). These and other scenarios may be compatible with the techniques presented herein.

E2. Stack Order

A second aspect that may vary among embodiments of these techniques involves the tack order 112 of the stack 106 of unit boxes 108. For example, the stack order 112 may represent a date 130 associated with the unit boxes 108, such as a date of creation or access of the unit box 108. Alternatively, the stack order 112 may be selected according to one or more categories of the unit boxes 108 (e.g., the unit boxes 108 of a first category may be ordered in the stack order 112 before the unit boxes 108 of a second category). The stack order 112 may also be user-selectable; e.g., the user 102 may be permitted to select a stack order 112 for the stack 106, and the unit boxes 108 may be reordered according to the selected stack order 112. Alternatively or additionally, the unit boxes 108 may be grouped within the stack order 112; e.g., a first set of unit boxes 108 in a first category may be presented as a first group before a second set of unit boxes 108 in a second category.

E3. Stack Presentation, Navigation, and Transitions

A third aspect that may vary among embodiments of these techniques relates to the manner of enabling gestures to navigate within the stack 106, and the transitions presenting such gestures and navigation.

As a first variation of this third aspect, the presentation of the stack 106 may include an indication of the stack position 116 within the stack. For example, a stack indicator may be embedded in the presentation of the unit box 108 showing both the number of unit boxes 108 in the stack 106 and the position of the current unit box 118 in the stack 106.

As a second variation of this third aspect, a unit box 108 may comprise a first unit box half and a second unit box half respectively arranged along the first axis 124 (e.g., a right half and a left half of the unit box 108 providing "one-half unit box operations"). The first unit box half may be oriented in the forward direction 126 along the first axis 124 with respect to the second unit box half (e.g., the first unit box half may be positioned to the right of the second unit box half where the forward direction 126 is rightward), such that the forward gesture may comprise a selection of the first unit box half (e.g., tapping on the right half of the unit box or sliding to the right), and the backward gesture comprising a selection of the second unit box half.

As a third variation of this third aspect, various types of visual transitions may assist the user 102 in understanding the navigation within the stack 106. For example, transitioning from the current unit box 118 to the next unit box may comprise presenting a forward slide animation along the forward direction 126 of the first axis 124, where the forward slide replaces the current unit box 118 with the next unit box. Conversely, transitioning from the current unit box 118 to the preceding unit box may comprise presenting a back slide animation opposite the forward direction 126 of the first axis 124, and replacing the current unit box 118 with the preceding unit box.

As a fourth variation of this third aspect, additional gestures may be provided that enable additional navigation within the stack 106. For example, a second axis may be defined that is orthogonal with the first axis 124, such that gestures provided along the second axis enable additional types of navigation, or may provide data entry in the form of a selection among a set of options. As one such example, upon receiving a change gesture along a second axis that is orthogonal with the first axis 124, the device 104 may identify a selected icon in the unit box 108 that is near the change gesture; identify an alternative item for the item 110 of the unit box 108 represented the selected icon; and transition from the selected item to the alternative item in the unit box 108. As one such example, where the unit box 108 comprises at least two unit box portions respectively arranged along the first axis 124, and where respective items 110 of the unit box 1089 may be presented in a unit box portion, the item change slide animation may involve presenting a unit box portion transition along the second axis replacing the unit box portion presenting the selected item with an alternative unit box portion presenting the alternative item. This transition may affect the contents of the unit box 108; e.g., the alternative item may comprise a replacement item for the selected item that, upon receiving the change gesture, replaces the selected item in a record stored in the memory representing the unit box. Moreover, such selection may be conditioned upon an acceptance by the user 102; e.g., the alternative item comprising a second option selected from an option set including the selected item that, upon subsequently receiving an accepting gesture, replaces the selected item in a record stored in the memory representing the unit box. As another example, the unit box 108 may be associated with a second stack that is associated with an item type and comprising at least two unit boxes 108 respectively comprising a second stack item associated with the item type (e.g., the item type comprising a unit box category, and the second stack may comprise the unit boxes 108 of the stack 106 that are associated with the unit box category). In this example, the transitioning from the selected item to the alternative item 110 in the unit box 108 may involve transitioning from the selected item 110 associated with the item type to the second stack item of another unit box 108 in the second stack that is associated with the item type. Many such navigation features may be compatible with the techniques presented herein.

Figure 5:
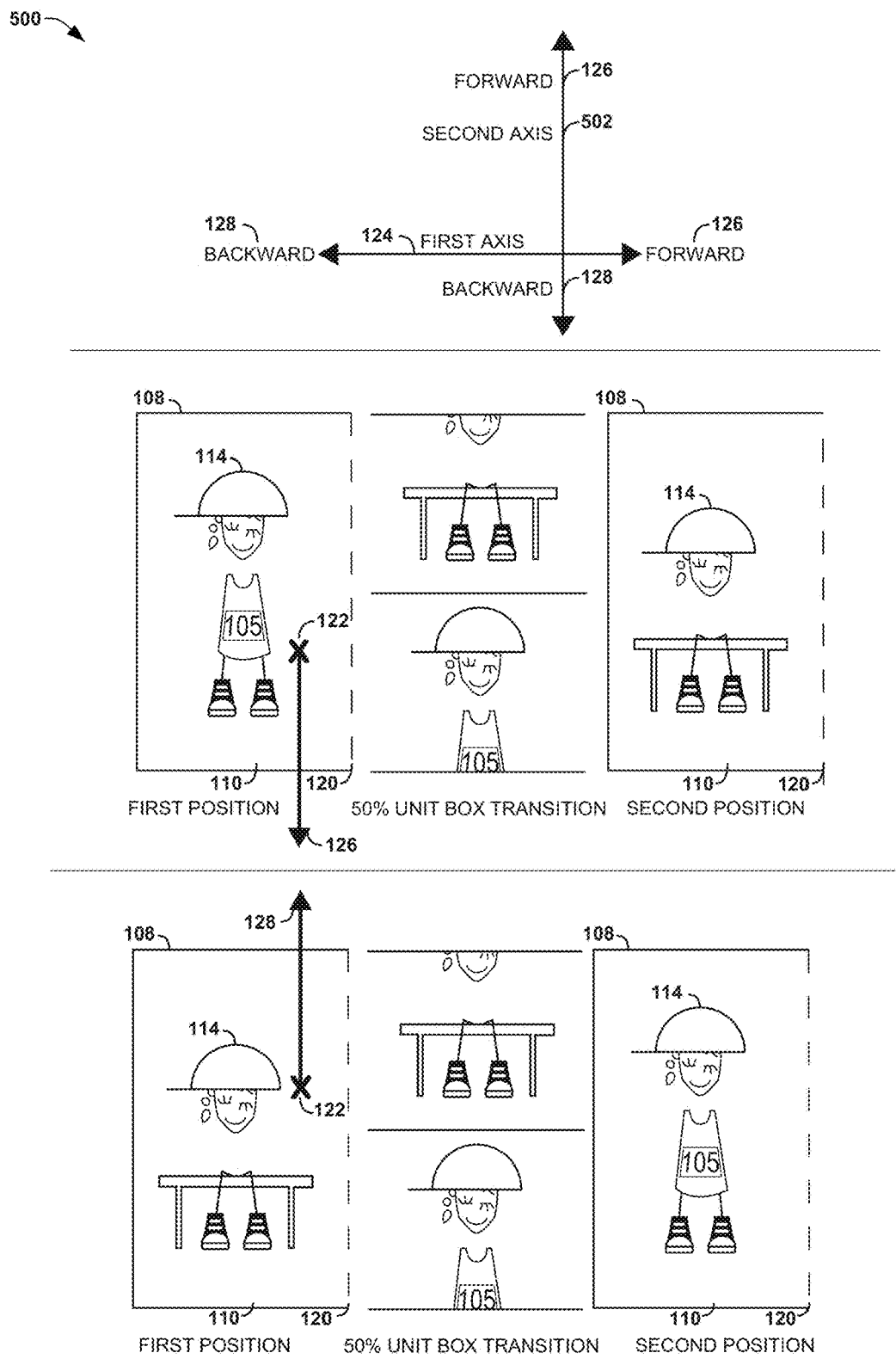
FIG. 5 is an illustration of an exemplary scenario featuring a selection of an option within a unit box user interface.

FIG. 5 presents an illustration of an exemplary scenario 500 featuring one such navigation. In this exemplary scenario 500, a unit box 108 is presented comprising a set of icons 114 representing respective items 110 in a health record of an individual. A first axis 124 may be defined that enables navigation within the stack 106. Additionally, a second axis 502 comprising a forward direction 126 and a backward direction 128 (e.g., a vertical axis of the display to correspond with a horizontal axis of the display selected as the first axis 120). Respective portions (e.g., halves) of the unit box that are arrayed along the first axis may be navigated using gestures 122 provided along the second axis 502. For example, a gesture 122 provided in a forward direction 126 (e.g., an upward direction) along the second axis 502 on a left half of the unit box 108 may result in a transition from a first icon 114 representing a first option for the item 110 represented in this position of the unit box 108 to a second icon 114 representing a second option for the item 110 of the unit box 108. The selection may also be presented, e.g., an item change slide animation along the second axis that replacing the selected item with the alternative item in the unit box 108 (e.g., sliding the left half of the unit box 108 in an upward or downward direction along the second axis to replace the icon 114 representing a current selection for the item 110 of the unit box 108 with an icon 114 representing a different selection). Additionally, a gesture 122 provided in a backward direction 128 (e.g., a downward direction) along the second axis 502 on the left half of the unit box 108 may result in a transition in the opposite direction among the icons 114 representing the options for this portion of the unit box 108, e.g., a navigation from the second icon 114 back to the first icon 114. Additionally, such navigation operations may be presented to the user 102 with a visual transition (e.g., vertically sliding the new icon 114 in to replace the preceding icon 114). In this manner, gestures 122 provided along the second axis 502 may enable additional navigation options among the items 110 depicted in the unit box 108.

As a fifth variation of this third aspect, the stack 106 may comprise a sequence of at least two unit boxes 108 having a sequential order (e.g., a relationship among two or more unit boxes 108 of the stack 106). Upon receiving a user request to present the sequence, the device 104 may concurrently present on the display, for respective unit boxes 108 of the sequence, an icon 114 depicting an item of the unit box 108, where the icons 114 are arranged along the first axis 124 according to the sequential order of the sequence. Moreover, the icons 108 of the sequence may be arranged on the first axis 124 in a manner exceeding a first axis display dimension of the display (e.g., the sequence of icons 108 may be wider than the width of the display). The device 104 may present the icons 114 at a current sequence location; upon receiving a forward gesture while presenting the sequence, transition the current sequence location forward in the sequence; and upon receiving a backward gesture while presenting the sequence, transition the current sequence location backward in the sequence.

Figure 6:
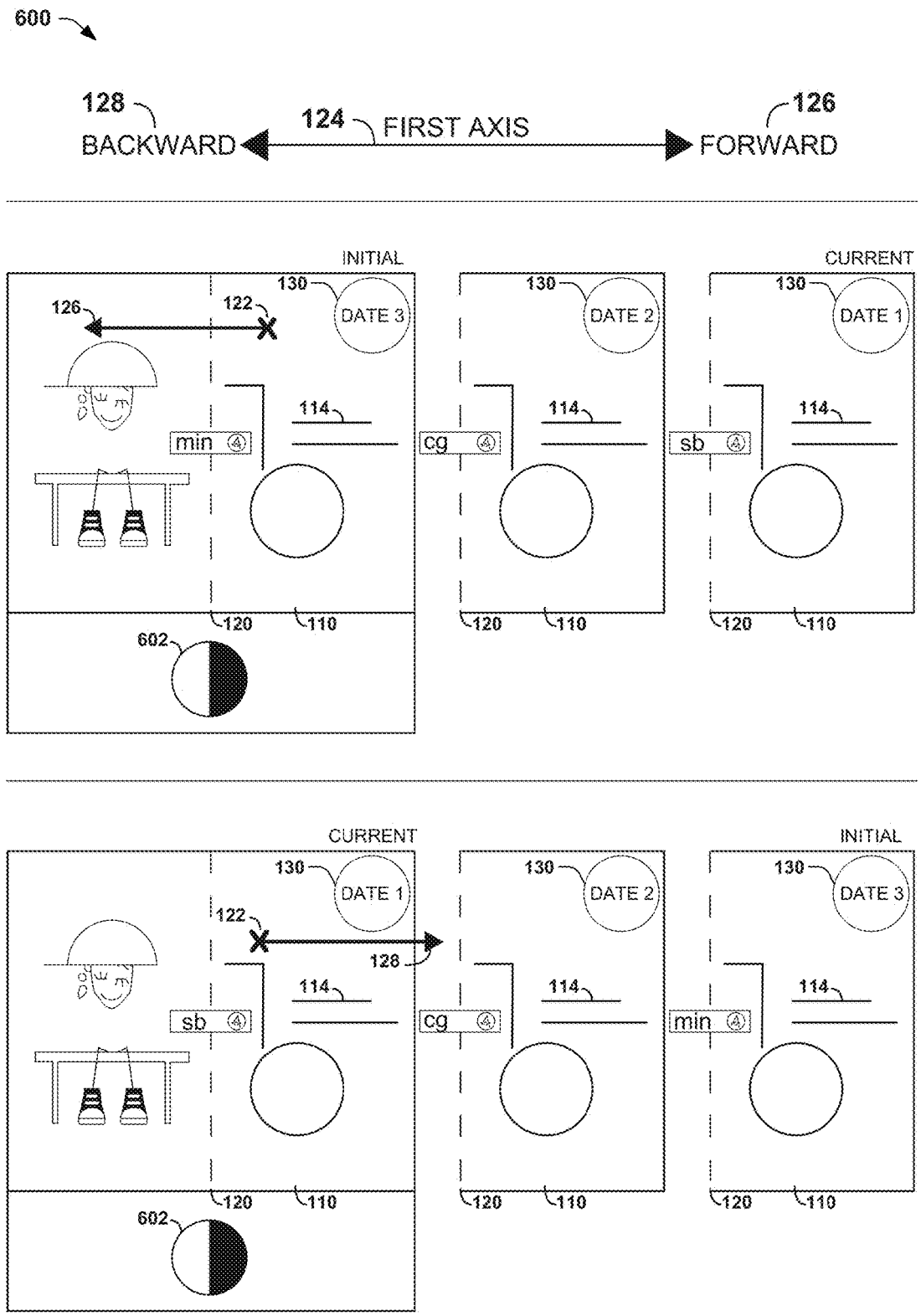
FIG. 6 is an illustration of an exemplary scenario featuring a drill-down operation provided for a unit box interface.

FIG. 6 presents an illustration of an exemplary scenario 600 featuring this type of navigation, wherein, among the unit boxes 108 of the stack 106, some unit boxes 108 may comprise a history for a particular activity in a category, such as a history of wheelchair "transfers" health records. A history control 602 embedded within the unit box 108 may be toggled by the user 102 to result in navigation options (e.g., along the second axis 502) in a manner that navigates within the sequence representing the history of the unit boxes 108 within this activity. For example, a gesture 122 provided in a forward direction 126 along the second axis 502, while the history control 602 is toggled, may result in a navigation from a current unit box 108 to a next unit box in the chronological order of unit boxes 108 within this category. Similarly, a gesture 122 provided in a backward direction 128 along the second axis 502, while the history control 602 is toggled, may result in a navigation from a current unit box 108 to a preceding unit box in the chronological order of unit boxes 108 within this activity. It may be additionally advantageous to present a visual transition depicting these navigation operations, and optionally using a different visual transition as for presenting other navigations within the unit boxes 108 (e.g., using a slide transition for selecting options among the portions of the unit box 108 when the history control 602 is not toggled, such as illustrated in the exemplary scenario 500 of FIG. 5; and using a fade transition to fade from a first icon 114 to a second icon 114 to illustrate the chronological navigation when the history control 602 is toggled). In this manner, gestures 122 may be interpreted to enable a second type of navigation among the portions of the unit boxes 108 in accordance with the techniques presented herein.

As a sixth variation of this third aspect, the presentation of the stack 106 may enable the creation of new unit boxes 108. As one such example, for at least one item 110 that is ordinarily presented in a unit box location of the unit box 108, a request for a new unit box (e.g., a cloning of a previously generated unit box 108) may cause the device 104 to present the new unit box 104 by refraining from presenting an icon 114 for the item 110 in the unit box location, resulting in a blank area that solicits data entry for this item 110 from the user 102. Upon receiving a selection of the unit box location (e.g., tapping in the blank area), the device 104 may present icons 108 depicting at least two options in an option set for the item 110; and upon receiving a selection of a selected icon 114, the device 104 may create in the stack 106 a new unit box 108 comprising, for the item 110, the option associated with the selected icon 114. Additional gestures may be provided that alter the contents of the stack 106. For example, upon receiving a gesture toward an edge of the unit box in a removal direction, such as a downward direction toward a bottom edge of the display of the device), the device 104 may remove the unit box from the stack.

Figure 7:
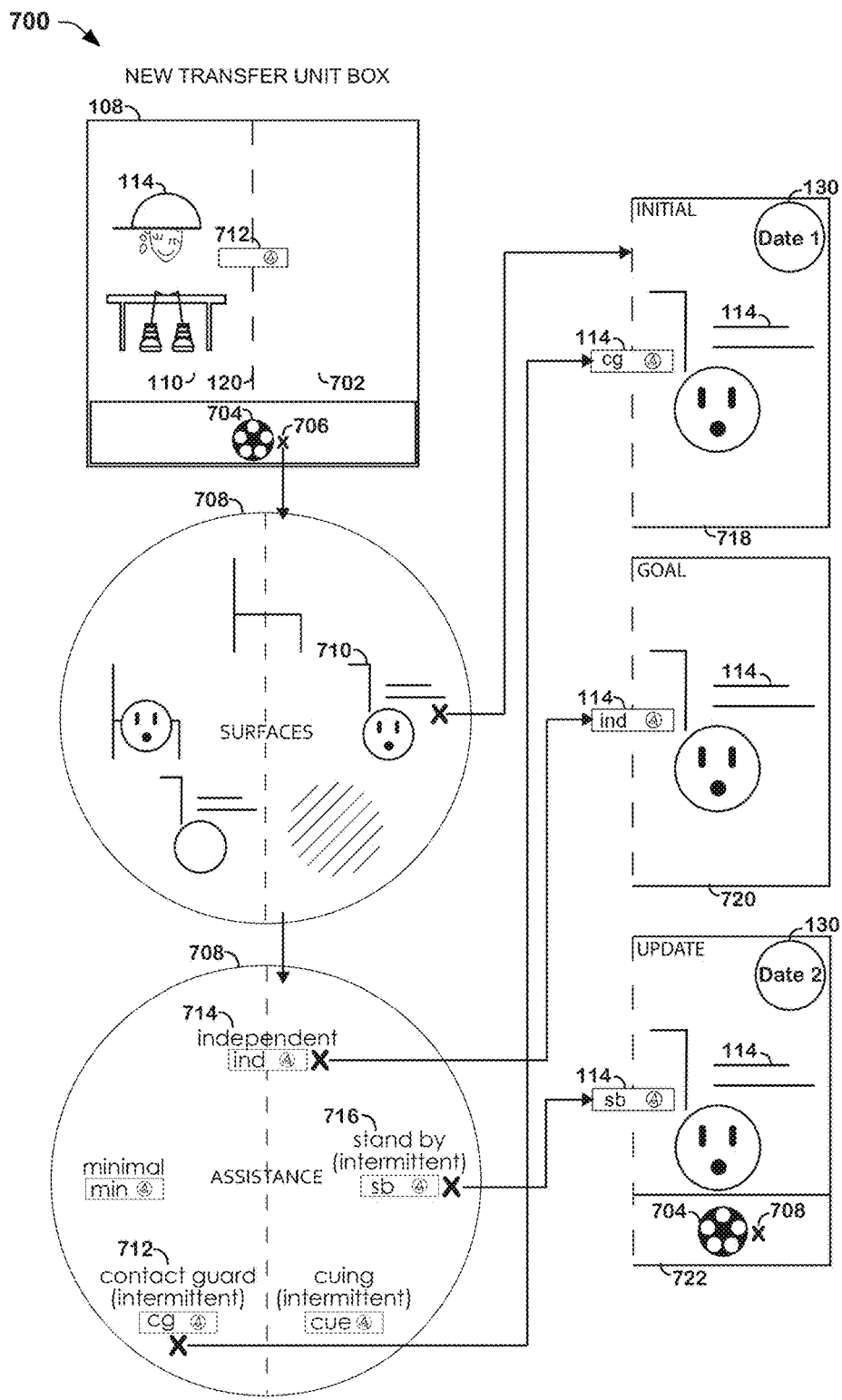
FIG. 7 is an illustration of an exemplary scenario featuring a selection of an option within a unit box interface.

FIG. 7 presents an illustration of an exemplary scenario 700 featuring a first example of data entry according to this variation. In this exemplary scenario 700, the device 104 receives a request to generate a new activity in unit box 108, create a goal, and then optionally update (clone) a previously created unit box, by identifying an item 110 that may be a subject of data entry for the cloned unit box 108. The device 104 therefore presents a blank area 702 in a unit box location that is ordinarily occupied by an icon 114 or indicator representing the item 110 for this unit box 108. The unit box 108 may also include ratings indicating the proficiency of the individual in performing the activity represented by the unit box 108 (e.g., a first option 712 indicating a contact guard proficiency; a second option 714 indicating an independent proficiency; and a third option 716 indicating a standby or intermittent proficiency), and/or a date 130 representing the date on which the activity represented by the unit box 110 was performed, observed, or reported. The device 104 may also present a palette icon 704 indicating an availability of options 710 for this blank area 702. Upon receiving a selection 706 of the palette icon 704, the device 104 may present a palette 704 comprising icons 114 representing the options 710 for this item 110 of the unit box 108, including a first option 710 representing an independent proficiency; a second option 710 representing a standby proficiency; and a third option 710 representing a contact guard proficiency. Upon receiving a selection of an option 710 the device 104 may present the icon 114 or indicator in the previously blank area 702 of the unit box 108 (e.g., in order to select a proficiency for an initial unit box 718, a goal unit box 720, and/or an update unit box 722). A second selection 706 of the palette icon 704 for the new unit box 108 may result in a second presentation of the palette 708 enabling a second selection of an option 710 to create an additional unit box 108, etc. In this manner, the device 104 may enable the receipt of information for new unit boxes 108 in a manner that is consistent and compatible with the user interface techniques presented herein.

Figure 8:
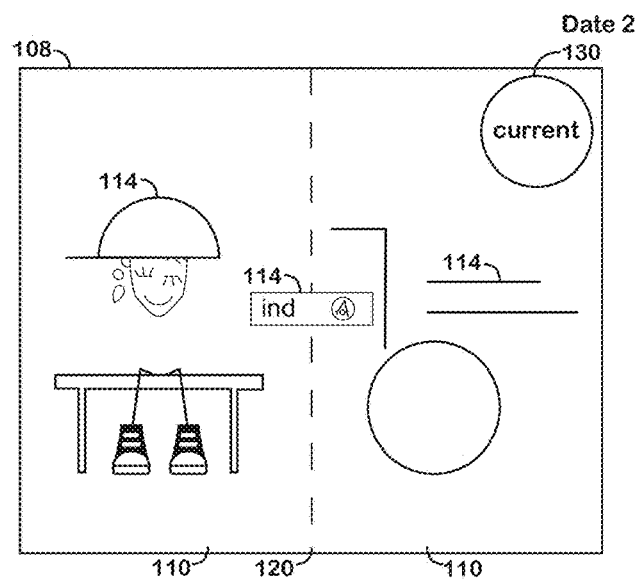
FIG. 8 is an illustration of an exemplary scenario featuring a stack operation enabled by a specific gesture within a unit box interface.
Figure 8:
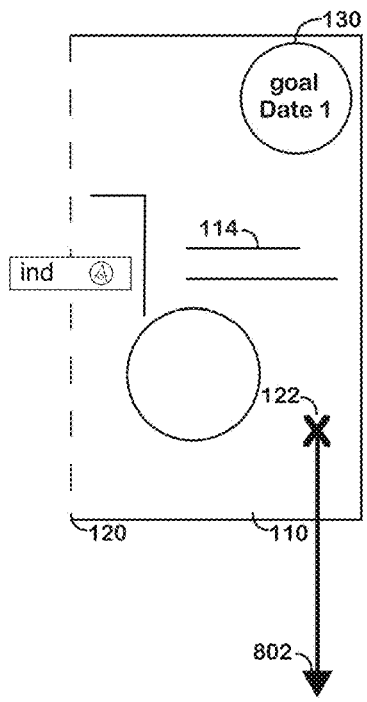

FIG. 8 presents an illustration an exemplary scenario 800 featuring a second example of data entry according to this variation. In this exemplary scenario 800, a unit box 108 is presented representing an activity that is a current target of therapeutic focus. A removal direction 802 may be defined, such as a downward direction toward an edge of the display of the device 104, such that a gesture 122 initiated on the unit box 108 and provided in the removal direction 902 may cause the device 104 to remove the unit box 108 from the stack 106. Optionally, a visual transition may be included to depict the operation on the stack 106 for the user 102, e.g., fading out the icon 114 in a right half of the unit box 108. In this manner, specific gestures 122 may enable stack operations other than navigation in accordance with the techniques presented herein.

As a seventh variation of this third aspect, at least one item 110 of the unit box 108 may comprise a current status of an individual, and the unit box 108 may be associated with a target status. The device 104 may be further configured to present the target status on the display adjacent to the current status.

As an eighth variation of this third aspect, where the stack 106 comprises at least one additional unit box 108 other than the selected unit box 108, the device 104 may be configured to, for respective additional unit boxes 108, while presenting the unit box 108 on the display, concurrently present a description of the additional unit box 108, including the stack order of the unit boxes in the stack 106. These and other features may be included in implementations of the graphical user interface in accordance with the techniques presented herein.

F. Computing Environment

Figure 9:
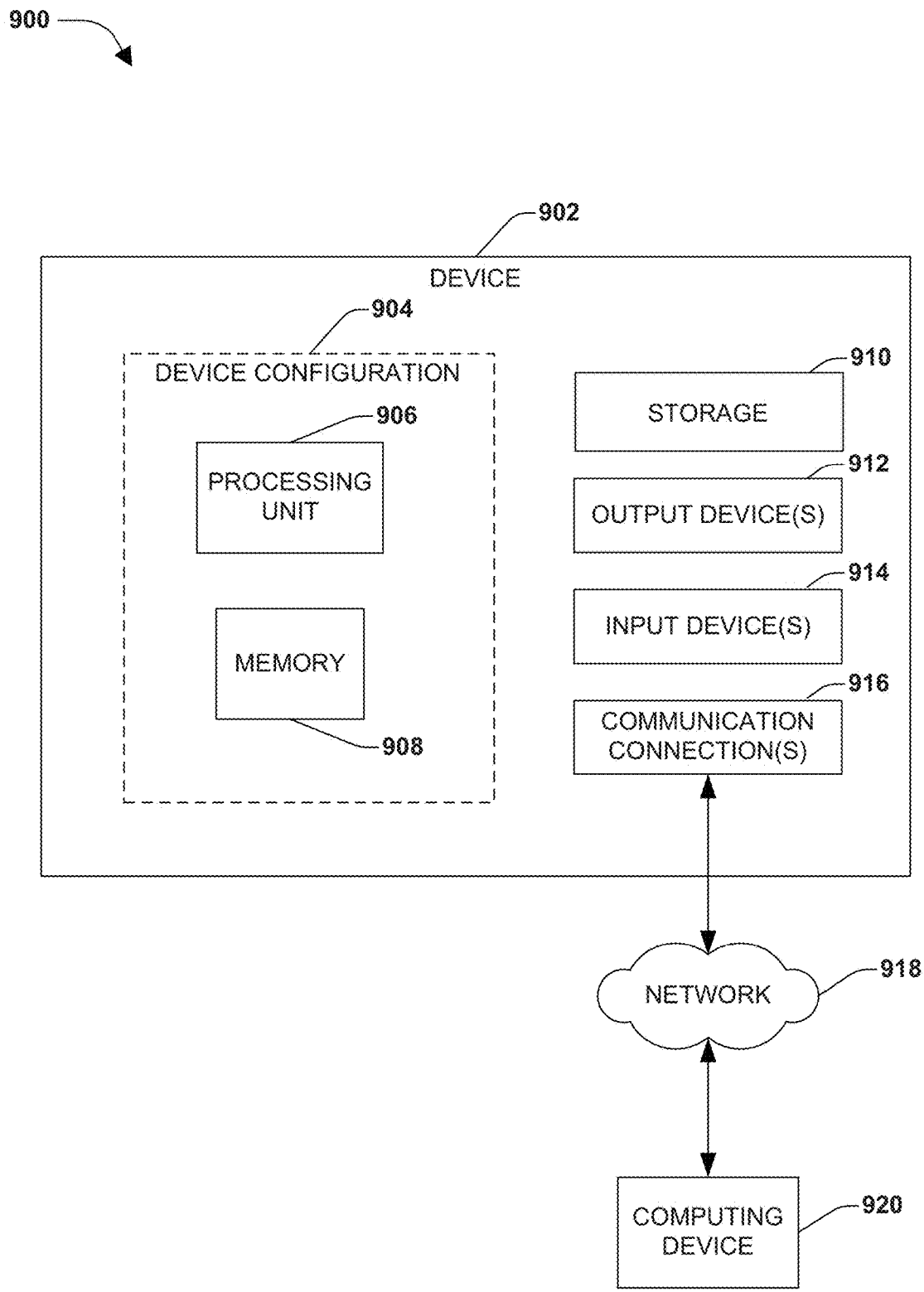
FIG. 9 is an illustration of an exemplary computing environment wherein the techniques provided herein may be utilized.

FIG. 9 and the following discussion provide a brief, general description of a suitable computing environment to implement embodiments of one or more of the provisions set forth herein. The operating environment of FIG. 9 is only one example of a suitable operating environment and is not intended to suggest any limitation as to the scope of use or functionality of the operating environment. Example computing devices include, but are not limited to, personal computers, server computers, hand-held or laptop devices, mobile devices (such as mobile phones, Personal Digital Assistants (PDAs), media players, and the like), multiprocessor systems, consumer electronics, mini computers, mainframe computers, distributed computing environments that include any of the above systems or devices, and the like.

Although not required, embodiments are described in the general context of "computer readable instructions" being executed by one or more computing devices. Computer readable instructions may be distributed via computer readable media (discussed below). Computer readable instructions may be implemented as program modules, such as functions, objects, Application Programming Interfaces (APIs), data structures, and the like, that perform particular tasks or implement particular abstract data types. Typically, the functionality of the computer readable instructions may be combined or distributed as desired in various environments.

FIG. 9 illustrates an example of a system 900 comprising a computing device 902 configured to implement one or more embodiments provided herein. In one configuration, computing device 902 includes at least one processing unit 906 and memory 908. Depending on the exact configuration and type of computing device, memory 908 may be volatile (such as RAM, for example), non-volatile (such as ROM, flash memory, etc., for example) or some combination of the two. This configuration is illustrated in FIG. 9 by dashed line 904.

In other embodiments, device 902 may include additional features and/or functionality. For example, device 902 may also include additional storage (e.g., removable and/or non-removable) including, but not limited to, magnetic storage, optical storage, and the like. Such additional storage is illustrated in FIG. 9 by storage 910. In one embodiment, computer readable instructions to implement one or more embodiments provided herein may be in storage 910. Storage 910 may also store other computer readable instructions to implement an operating system, an application program, and the like. Computer readable instructions may be loaded in memory 908 for execution by processing unit 906, for example.

The term "computer readable media" as used herein includes computer storage media. Computer storage media includes volatile and nonvolatile, removable and non-removable media implemented in any method or technology for storage of information such as computer readable instructions or other data. Memory 908 and storage 910 are examples of computer storage media. Computer storage media includes, but is not limited to, RAM, ROM, EEPROM, flash memory or other memory technology, CD-ROM, Digital Versatile Disks (DVDs) or other optical storage, magnetic cassettes, magnetic tape, magnetic disk storage or other magnetic storage devices, or any other medium which can be used to store the desired information and which can be accessed by device 902. Any such computer storage media may be part of device 902.

Device 902 may also include communication connection(s) 916 that allows device 902 to communicate with other devices. Communication connection(s) 916 may include, but is not limited to, a modem, a Network Interface Card (NIC), an integrated network interface, a radio frequency transmitter/receiver, an infrared port, a USB connection, or other interfaces for connecting computing device 902 to other computing devices. Communication connection(s) 916 may include a wired connection or a wireless connection. Communication connection(s) 916 may transmit and/or receive communication media.

The term "computer readable media" may include communication media. Communication media typically embodies computer readable instructions or other data in a "modulated data signal" such as a carrier wave or other transport mechanism and includes any information delivery media. The term "modulated data signal" may include a signal that has one or more of its characteristics set or changed in such a manner as to encode information in the signal.

Device 902 may include input device(s) 914 such as keyboard, mouse, pen, voice input device, touch input device, infrared cameras, video input devices, and/or any other input device. Output device(s) 912 such as one or more displays, speakers, printers, and/or any other output device may also be included in device 902. Input device(s) 914 and output device(s) 912 may be connected to device 902 via a wired connection, wireless connection, or any combination thereof. In one embodiment, an input device or an output device from another computing device may be used as input device(s) 914 or output device(s) 912 for computing device 902.

Components of computing device 902 may be connected by various interconnects, such as a bus. Such interconnects may include a Peripheral Component Interconnect (PCI), such as PCI Express, a Universal Serial Bus (USB), Firewire (IEEE 1394), an optical bus structure, and the like. In another embodiment, components of computing device 902 may be interconnected by a network. For example, memory 908 may be comprised of multiple physical memory units located in different physical locations interconnected by a network.

Those skilled in the art will realize that storage devices utilized to store computer readable instructions may be distributed across a network. For example, a computing device 920 accessible via network 918 may store computer readable instructions to implement one or more embodiments provided herein. Computing device 902 may access computing device 920 and download a part or all of the computer readable instructions for execution. Alternatively, computing device 902 may download pieces of the computer readable instructions, as needed, or some instructions may be executed at computing device 902 and some at computing device 920.

G. Usage of Terms

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used in this application, the terms "component," "module," "system", "interface", and the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

Various operations of embodiments are provided herein. In one embodiment, one or more of the operations described may constitute computer readable instructions stored on one or more computer readable media, which if executed by a computing device, will cause the computing device to perform the operations described. The order in which some or all of the operations are described should not be construed as to imply that these operations are necessarily order dependent. Alternative ordering will be appreciated by one skilled in the art having the benefit of this description. Further, it will be understood that not all operations are necessarily present in each embodiment provided herein.

Moreover, the word "exemplary" is used herein to mean serving as an example, instance, or illustration. Any aspect or design described herein as "exemplary" is not necessarily to be construed as advantageous over other aspects or designs. Rather, use of the word exemplary is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated exemplary implementations of the disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. A nonvolatile computer-readable storage device comprising instructions that, when executed on a processor of a device having a display and a memory, present stack of unit boxes having a stack order, respective unit boxes comprising a first area, a second area, and at least one items, by:
for a current unit box in the stack, present on the display a unit box comprising at least one icon respectively depicting an item of the unit box;
upon receiving a selection of the first area, transitioning from the current unit box to a next unit box after the current unit box in the stack order, and displaying a unit box corresponding to the next unit box, the next unit box comprising at least one icon respectively depicting an item of the next unit box; and
upon receiving a selection of the second area, transitioning from the current unit box to a preceding unit box before the current unit box in the stack order, and displaying a unit box corresponding to the preceding unit box, the preceding unit box comprising at least one icon respectively depicting an item of the preceding unit box.

2. A system for presenting, on a device having a processor, a display, and a memory storing an icon set, a stack of unit boxes having a stack order, respective unit boxes comprising at least one item, the system comprising:
a unit box presenting component comprising instructions stored in the memory that, when executed on the processor, cause the device to, for a current unit box in the stack, present on the display a unit box and comprising at least one icon respectively depicting an item of the unit box, the unit box further comprising a first area and a second area; and
a stack navigating component comprising instructions stored in the memory that, when executed on the processor, cause the device to:
upon receiving a selection associated with the first area of the unit box, transition from the current unit box to a next unit box after the current unit box in the stack order, and displaying a unit box corresponding to the next unit box, the next unit box comprising at least one icon respectively depicting an item of the next unit box; and
upon receiving a selection associated with the second area of the unit box, transition from the current unit box to a preceding unit box before the current unit box in the stack order, and displaying a unit box corresponding to the preceding unit box, the preceding unit box comprising at least one icon respectively depicting an item of the preceding unit box.

3. A method of presenting a stack of unit boxes having a stack order, respective unit boxes comprising at least one item on a device having a processor, a display, and a memory storing an icon set, the method comprising:
executing on the processor instructions configured to:
for a current unit box in the stack, presenting on the display a unit box comprising at least one icon respectively depicting an item of the unit box;
upon receiving a forward gesture associated with a first axis in a forward direction, transitioning from the current unit box to a next unit box after the current unit box in the stack order, and presenting on the display a unit box comprising at least one icon depicting an item of the next unit box;
upon receiving a backward gesture associated with the first axis opposite the forward direction, transitioning from the current unit box to a preceding unit box before the current unit box in the stack order, and presenting on the display a unit box comprising at least one icon depicting an item of the preceding unit box;
upon receiving a change gesture along a second axis that is orthogonal with the first axis:
identifying a selected item in a currently displayed unit box that is near the change gesture;
identifying an alternative item for the selected item;
transitioning from the selected item to the alternative item in the unit box, and displaying the alternative item in the currently displayed unit box.

4. The method of claim 3:
the unit box comprising a first unit box half and a second unit box half respectively arranged along the first axis, the first unit box half oriented in the forward direction along the axis with respect to the second unit box half;
the forward gesture comprising a selection of the first unit box half; and the backward gesture comprising a selection of the second unit box half.

5. The method of claim 3, transitioning from the current unit box to the next unit box comprising: presenting a forward slide animation along the forward direction of the first axis replacing the current unit box with the next unit box.

6. The method of claim 3, transitioning from the current unit box to the preceding unit box comprising: presenting a back slide animation opposite the forward direction of the first axis replacing the current unit box with the preceding unit box.

7. The method of claim 3:
respective unit boxes associated with a date; and
the stack ordering the unit boxes according to the dates.

8. The method of claim 3, transitioning from the selected item to the alternative item comprising: presenting an item change slide animation along the second axis replacing the selected item with the alternative item.

9. The method of claim 8:
the unit box comprising at least two unit box portions respectively arranged along the first axis;
respective items of the unit box presented in a unit box portion; and
presenting the item change slide animation comprising: presenting a unit box portion transition along the second axis replacing the unit box portion presenting the selected item with an alternative unit box portion presenting the alternative item.

10. The method of claim 3, the alternative item comprising a replacement item for the selected item that, upon receiving the change gesture, replaces the selected item in a record stored in the memory representing the unit box.

11. The method of claim 3, the alternative item comprising a second option selected from an option set including the selected item that, upon subsequently receiving an accepting gesture, replaces the selected item in a record stored in the memory representing the unit box.

12. The method of claim 3:
the unit box associated with a second stack associated with an item type and comprising at least two unit boxes respectively comprising a second stack item associated with the item type; and
transitioning from the selected item to the alternative item in the unit box comprising: transitioning from the selected item associated with the item type to the second stack item of another unit box in the second stack that is associated with the item type.

13. The method of claim 12:
the item type comprising a unit box category; and
the second stack comprising the unit boxes of the stack that are associated with the unit box category.

14. The method of claim 3, the instructions further configured to:
for at least one item ordinarily presented in a unit box location, refrain from presenting an icon for the item in the unit box location; and
upon receiving a selection of the unit box location:
present icons depicting at least one option in an option set for the item; and
upon receiving a selection of a selected icon, create in the stack a new unit box comprising, for the item, the option associated with the selected icon.

15. The method of claim 3:
at least one item of the unit box comprising a current status; the unit box associated with a target status; and
the instructions further configured to present the target status on the display adjacent to the current status.

16. The method of claim 3:
the stack comprising a sequence of at least two unit boxes, the sequence having a sequential order; and
the instructions further configured to, upon receiving a user request to present the sequence, concurrently present on the display, for respective unit boxes of the sequence, an icon depicting an item of the unit box, the icons arranged along the first axis according to the sequential order of the sequence.

17. The method of claim 16:
the icons of the sequence arranged on the first axis exceeding a first axis display dimension of the display; and
the instructions further configured to:
present the icons at a current sequence location;
upon receiving a forward gesture while presenting the sequence, transition the current sequence location forward in the sequence; and
upon receiving a backward gesture while presenting the sequence, transition the current sequence location backward in the sequence.

18. The method of claim 3:
the stack comprising at least one additional unit box other than the selected unit box; and
the instructions further configured to, for respective additional unit boxes, while presenting the unit box on the display, concurrently present a description of the additional unit box.

19. The method of claim 3, the instructions further configured to, upon receiving a gesture toward an edge of the unit box in a removal direction, remove the unit box from the stack.

20. A nonvolatile computer-readable storage device comprising instructions that, when executed on a processor of a device having a display and a memory, present stack of unit boxes having a stack order, respective unit boxes comprising at least one items, by:
for a current unit box in the stack, present on the display a unit box comprising textual data for an item of the unit box;
upon receiving a forward gesture associated with a first axis in a forward direction, transition from the current unit box to a next unit box after the current unit box in the stack order, and presenting on the display a unit box comprising at least one icon depicting an item of the next unit box;
upon receiving a backward gesture associated with the first axis opposite the forward direction, transition from the current unit box to a preceding unit box before the current unit box in the stack order and presenting on the display a unit box comprising at least one icon depicting an item of the preceding unit box; and
upon receiving a change gesture along a second axis that is orthogonal with the first axis:
identify a selected item in a currently displayed unit box that is near the change gesture;
identify an alternative item for the selected item;
transition from the selected item to the alternative item in the unit box, and
display the alternative item in the currently displayed unit box.

21. A nonvolatile computer-readable storage device comprising instructions that, when executed on a processor of a device having a display and a memory, present stack of unit boxes associated with categories of medical records, the unit boxes having a stack order, respective unit boxes comprising at least one items, by:
for a current unit box in the stack, present on the display a unit box comprising an image representative of a category of the unit box and an image representative of an activity;
upon receiving a forward gesture associated with a first axis in a forward direction, transitioning from the current unit box to a next unit box after the current unit box in the stack order and present on the display an image representative of a category for the next unit box and an image representative of an activity;
upon receiving a backward gesture associated with the first axis opposite the forward direction, transitioning from the current unit box to a preceding unit box before the current unit box in the stack order, and present on the display an image representative of a category for the next unit box and an image representative of an activity; and
upon receiving a change gesture along a second axis that is orthogonal with the first axis:
identify a selected activity in a currently displayed unit box that is near the change gesture;
identify an alternative activity for the selected item;
transition from the selected activity to the alternative activity in the unit box, and display the alternative activity in the currently displayed unit box.

22. The computer readable storage device of claim 1, wherein the first area is a right side of the unit box and the second area is a left side of the unit box.

23. The computer readable medium of storage device of claim 22, wherein the at least one icon represents a category of data;
the unit box further comprises a change button; and
wherein selection of the change button changes the category of the unit box.

* * * * *